US012694969B2

(12) United States Patent
Takemura et al.

(10) Patent No.: US 12,694,969 B2
(45) Date of Patent: Jul. 28, 2026

(54) IMAGE DISPLAY SYSTEM GENERATING DATA DISPLAYABLE ON CONVERTED MEDICAL IMAGE DATA

(71) Applicant: KONICA MINOLTA, INC., Tokyo (JP)

(72) Inventors: Tomoaki Takemura, Hachioji (JP); Hisashi Wada, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 518 days.

(21) Appl. No.: 18/137,540

(22) Filed: Apr. 21, 2023

(65) Prior Publication Data

US 2023/0402155 A1 Dec. 14, 2023

(30) Foreign Application Priority Data

Jun. 14, 2022 (JP) ................................ 2022-095918

(51) Int. Cl.
G16H 30/20 (2018.01)
G16H 30/40 (2018.01)

(52) U.S. Cl.
CPC ............. G16H 30/20 (2018.01); G16H 30/40 (2018.01)

(58) Field of Classification Search
CPC ........ G16H 30/20; G16H 30/40; G16H 15/00; G16H 40/67; G16H 50/20
USPC ....................................................... 382/128
See application file for complete search history.

(56) References Cited

U.S. PATENT DOCUMENTS 9,168,007 B2 10/2015 Ozaki et al.
2009/0080752 A1 3/2009 Ruth et al.

2009/0279753 A1* 11/2009 Sakaida ................. G06V 10/98
382/128
2010/0128950 A1 5/2010 Woods et al.
2012/0183188 A1* 7/2012 Moriya .................. G16H 30/20
382/128
2021/0216822 A1* 7/2021 Paik ........................ G10L 15/22
2021/0374948 A1* 12/2021 Jung ..................... G06T 7/0012
2024/0177836 A1* 5/2024 Paik ....................... A61B 5/742

FOREIGN PATENT DOCUMENTS

JP H09238934 A 9/1997
JP 2004180932 A 7/2004
JP 2012040044 A 3/2012
JP 2020529292 A 10/2020

OTHER PUBLICATIONS

Japanese Office Action (and an English language translation thereof) dated Oct. 1, 2024, issued in counterpart Japanese Application No. 2022-095918.
Japanese Office Action (and an English language translation thereof) dated Dec. 10, 2024, issued in counterpart Japanese Application No. 2022-095918.

* cited by examiner

*Primary Examiner* — Allen H Nguyen

(74) *Attorney, Agent, or Firm* — Holtz, Holtz & Volek PC

(57) ABSTRACT

An image display system includes a first hardware processor that: obtains an analysis result acquired by a computer process for first medical image data having a first slice thickness; obtains second medical image data reconstructed, from the first medical image data, to have a second slice thickness different from the first slice thickness; and converts the analysis result of the first medical image data into what is displayable on a second medical image based on the second medical image data.

12 Claims, 8 Drawing Sheets

FIG.6

| Thin No. | INSTANCE NUMBER | IMAGE POSITION(X,Y,Z) |
|---|---|---|
| Thin-1 | 1 | -160.0,160.0,-340.0 |
| Thin-2 | 2 | -160.0,160.0,-341.0 |
| Thin-3 | 3 | -160.0,160.0,-342.0 |
| ... | ... | ... |
| Thin-300 | 300 | -160.0,160.0,-640.0 |

FIG.7

| Thick No. | INSTANCE NUMBER | IMAGE POSITION(X,Y,Z) |
|---|---|---|
| Thick-1 | 1 | -160.0,160.0,-340.0 |
| Thick-2 | 2 | -160.0,160.0,-345.0 |
| Thick-3 | 3 | -160.0,160.0,-350.0 |
| ... | ... | ... |
| Thick-60 | 60 | -160.0,160.0,-640.0 |

FIG.8

| Thin No. | Thick No. |
|---|---|
| Thin-1 | Thick-1 |
| Thin-2 | Thick-1 |
| Thin-3 | Thick-1 |
| Thin-4 | Thick-1 |
| Thin-5 | Thick-1 |

| Thin No. | Thick No. |
|---|---|
| Thin-6 | Thick-2 |
| Thin-7 | Thick-2 |
| Thin-8 | Thick-2 |
| Thin-9 | Thick-2 |
| Thin-10 | Thick-2 |

...

| Thin No. | Thick No. |
|---|---|
| Thin-296 | Thick-60 |
| Thin-297 | Thick-60 |
| Thin-298 | Thick-60 |
| Thin-299 | Thick-60 |
| Thin-300 | Thick-60 |

IMAGE DISPLAY SYSTEM GENERATING DATA DISPLAYABLE ON CONVERTED MEDICAL IMAGE DATA

CROSS-REFERENCE TO RELATED APPLICATIONS

The entire disclosure of Japanese Patent Application No. 2022-095918 filed on Jun. 14, 2022 is incorporated herein by reference in its entirety.

TECHNICAL FIELD

The present invention relates to an image display system, an analysis apparatus, an image management apparatus, and a recording medium.

DESCRIPTION OF THE RELATED ART

For medical images made up of a plurality of slice images, such as CT images and MRI images, conventionally, in order to improve reading efficiency (a larger slice thickness allows faster reading) and to reduce the load on the storage capacity, reconstructed images having a large slice thickness (e.g. a thickness of 5 mm) are stored in a Picture Archiving and Communication System (PACS).

JP 2004-180932A describes a technique that detects a lesion candidate region from a CT image through computer aided diagnosis (CAD), and stores information on the detected lesion candidate region in association with a test identification number of a detection-source slice image and with an image number.

SUMMARY OF THE INVENTION

Incidentally, an analysis system that detects a lesion candidate region by a computer process, such as of CAD or artificial intelligence (AI), defines a specification for the slice thicknesses of input images, on a system-by-system basis. Analysis with a thinner-slice image (e.g., a thickness of 1 mm) being used as an input image has a higher analysis accuracy. Accordingly, to achieve an analysis performance, a specification of analysis using a thin-slice image (e.g., a thickness of 1 mm) as an input image is adopted.

Unfortunately, according to an analysis system conforming to a specification of analyzing thin-slice images (e.g., a thickness of 1 mm) as input images, only transmission of an analysis result (position information on and the feature amount of a lesion candidate region) achieved with thin-slice images (e.g., a thickness of 1 mm) to the PACS cannot associate the images with a reconstructed large slice thickness image (e.g., a thickness of 5 mm). Consequently, the analysis result cannot be displayed on the PACS side.

Conventionally, a reconstructed image having a large slice thickness (e.g., a thickness of 5 mm) is transmitted to the PACS and stored, and furthermore, in addition to the analysis result obtained with thin-slice images (e.g., a thickness of 1 mm), the thin-slice images (e.g., a thickness of 1 mm) used for the analysis are transmitted to the PACS side and stored for a prescribed time period, and the analysis result is displayed on the thin-slice images (e.g., a thickness of 1 mm). However, storing of all the images with the thin slice thickness on the PACS side requires a large capacity. Accordingly, after lapse of the prescribed time period, the images are removed in a time-dependent manner.

Unfortunately, if the thin-slice images used for the analysis am removed from the PACS, possible reconfirmation of the analysis result after the removal requires retransmission of the analysis result and the thin-slice images (e.g., a thickness of 1 mm) used for the analysis from the analysis system to the PACS, causing a problem of reducing the operation efficiency.

The present invention has been made in view of the problem described above, and has an object to allow an analysis result acquired by a computer process for first medical image data having a first slice thickness to be displayed on a second medical image reconstructed to have a second slice thickness different from the first slice thickness.

To achieve at least one of the abovementioned objects, according to an aspect of the present invention, an image display system reflecting one aspect of the present invention includes:

a first hardware processor that: obtains an analysis result acquired by a computer process for first medical image data having a first slice thickness;

obtains second medical image data reconstructed, from the first medical image data, to have a second slice thickness different from the first slice thickness; and converts the analysis result of the first medical image data into what is displayable on a second medical image based on the second medical image data.

To achieve at least one of the abovementioned objects, according to an aspect of the present invention, an image display system reflecting one aspect of the present invention includes:

a first hardware processor that outputs association information for convening an analysis result acquired by a computer process for first medical image data having a first slice thickness into what is displayable on a second medical image based on second medical image data reconstructed, from the first medical image data, to have a second slice thickness different from the first slice thickness.

To achieve at least one of the abovementioned objects, according to an aspect of the present invention, an analysis apparatus reflecting one aspect of the present invention includes:

a first hardware processor that: obtains an analysis result acquired by a computer process for first medical image data having a first slice thickness;

obtains second medical image data reconstructed, from the first medical image data, to have a second slice thickness different from the first slice thickness; and converts the analysis result of the first medical image data into what is displayable on a second medical image based on the second medical image data.

To achieve at least one of the abovementioned objects, according to an aspect of the present invention, an analysis apparatus reflecting one aspect of the present invention includes:

a first hardware processor that: obtains an analysis result acquired by a computer process for first medical image data having a first slice thickness;

obtains second medical image data reconstructed, from the first medical image data, to have a second slice thickness different from the first slice thickness; and outputs association information for converting the analysis result of the first medical image data into what is displayable on a second medical image based on the second medical image data.

To achieve at least one of the abovementioned objects, according to an aspect of the present invention, an analysis apparatus reflecting one aspect of the present invention includes:

a first hardware processor that outputs association information for converting an analysis result acquired by a computer process for first medical image data having a first slice thickness into what is displayable on a second medical image based on second medical image data reconstructed, from the first medical image data, to have a second slice thickness different from the first slice thickness.

To achieve at least one of the abovementioned objects, according to an aspect of the present invention, an image management apparatus reflecting one aspect of the present invention includes:

a second hardware processor that: obtains an analysis result acquired by a computer process for first medical image data having a first slice thickness;

obtains second medical image data reconstructed, from the first medical image data, to have a second slice thickness different from the first slice thickness; and converts the analysis result of the first medical image data into what is displayable on a second medical image based on the second medical image data.

To achieve at least one of the abovementioned objects, according to an aspect of the present invention, a recording medium reflecting one aspect of the present invention is a non-transitory computer readable recording medium storing a program causing a computer to perform:

obtaining an analysis result acquired by a computer process for first medical image data having a first slice thickness;

obtaining second medical image data reconstructed, from the first medical image data, to have a second slice thickness different from the first slice thickness; and converting the analysis result of the first medical image data into what is displayable on a second medical image based on the second medical image data.

To achieve at least one of the abovementioned objects, according to an aspect of the present invention, a recording medium reflecting one aspect of the present invention is a non-transitory computer readable recording medium storing a program causing a computer to perform outputting association information for converting an analysis result acquired by a computer process for first medical image data having a first slice thickness into what is displayable on a second medical image based on second medical image data reconstructed, from the first medical image data, to have a second slice thickness different from the first slice thickness.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 6 illustrates an association table that associates a combination between an instance number of and image position information on first medical image data with "Thin No. n";

FIG. 7 illustrates an association table that associates the combination between the instance number of and the image position information on second medical image data with "Thick No. m";

FIG. 8 illustrates an example of association information;

DETAILED DESCRIPTION

Hereinafter, one or more embodiments of the present invention will be described with reference to the drawings. However, the scope of the invention is not limited to the disclosed embodiments.

First Embodiment

[Configuration of Image Display System]

Figures 1, 2:
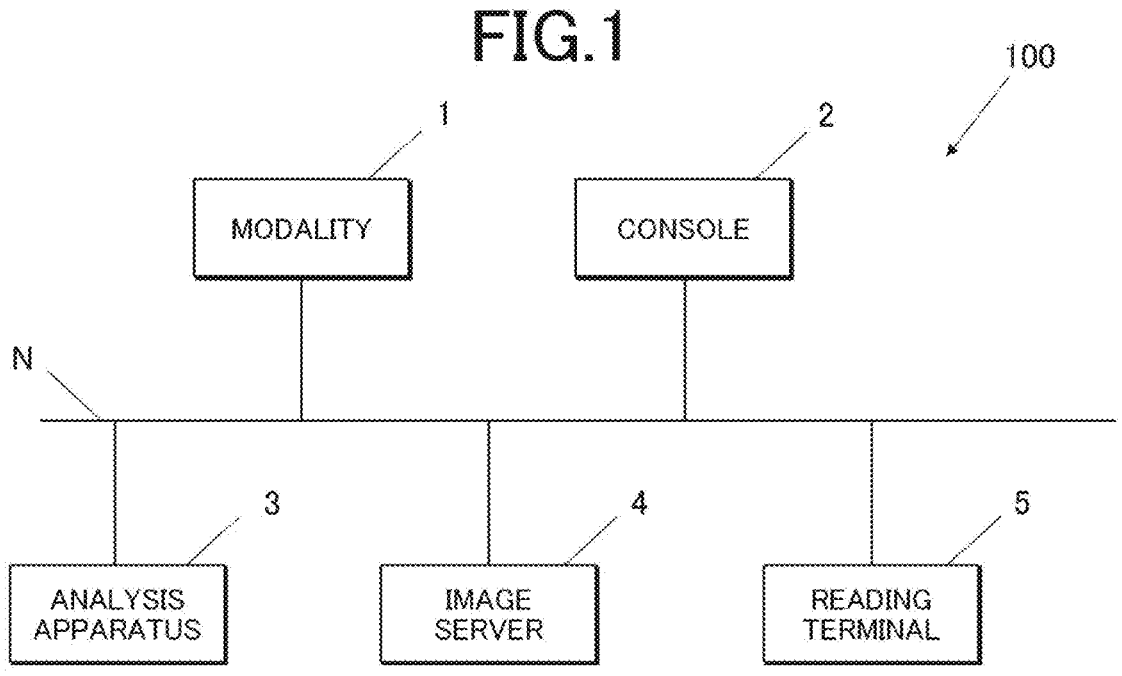
FIG. 1 is an entire configuration diagram of an image display system.
FIG. 2 is a diagram for illustrating coordinates of image position information.

FIG. 1 illustrates a system configuration example of an image display system 100 according to a first embodiment.

As illustrated in FIG. 1, the image display system 100 includes a modality 1, a console 2, an analysis apparatus 3, an image server 4, and a reading terminal 5, which are connected to each other via a communication network N, such as a local area network (LAN), a wide area network (WAN), or the Internet. The apparatuses that constitute the image display system 100 conform to the health level seven (HL7) and the digital image and communications in medicine (DICOM) standards, and communication between the apparatuses is performed in conformity with HL7 and DICOM. Note that the numbers of modalities 1, consoles 2, analysis apparatuses 3, reading terminals 5 and the like are not particularly limited.

The modality 1 is an image generation apparatus, such as of CT or an MRI, and images a test target site of a patient as an imaging subject and generates medical image data (medical image data including a plurality of slice image data items), based on test order information transmitted from an RIS (Radiology Information System), not illustrated, or the like. The modality 1 takes an image with a first slice thickness, and transmits acquired first medical image data having the first slice thickness, to the console 2. The first slice thickness is defined by a hospital in accordance with an imaging purpose and an imaging site, and is 1 mm in this embodiment.

The console 2 is an imaging control apparatus that includes a controller, a display, an operation receiver, a communicator, and a storage, which are not illustrated, and controls image taking in the modality 1. The console 2 outputs an imaging condition, and an image reading condition to the modality 1, and obtains first medical image data taken by the modality 1. The console 2 reconstructs the first medical image data obtained by the modality 1, and generates second medical image data having a second slice thickness thicker than the first slice thickness. The second slice thickness is defined by the hospital, and is 5 mm in this embodiment. The console 2 then writes, auxiliary information (patient information (patient ID, patient name, birth date, age, gender, height, weight, etc.), test information (test ID, test date, modality type, test site, visiting department, test purpose, etc.), image identification information (e.g., instance number, UID (Unique ID), etc.), and image position information, etc.), in each of the first medical image data and the second medical image data (for example, in a header of an image file of each slice) in conformity with the DICOM standard, and transmits the first medical image data and the second medical image data accompanied by the auxiliary information to the analysis apparatus 3 and transmits the second medical image data to an image server 4.

Here, the image position information includes an X coordinate, a Y coordinate, and a Z coordinate, as illustrated in FIG. 2. The X coordinate is a coordinate indicating a position in an X-axis direction illustrated in FIG. 2 (the width direction of a test subject M, and the lateral direction of a medical image). The Y coordinate is a coordinate indicating a position in a Y-axis direction illustrated in FIG. 2 (the body thickness direction of the test subject M, and the longitudinal direction of the medical image). The Z coordinate is a coordinate indicating a position in a Z-axis direction illustrated in FIG. 2 (the body axis direction of the test subject M, and the slice direction). Predetermined coordinates (e.g., the coordinates of the origin (top left point in the image)) are written as the X coordinate and the Y coordinate in the auxiliary information.

The instance number is a number indicating the order of a slice image data item in a series of first medical image data items (or second medical image data items). The UID is information for uniquely identifying the slice image data item.

The analysis apparatus 3 analyzes, by a computer process, the first medical image data transmitted from the console 2, detects a lesion candidate region, and transmits (outputs) an analysis result to the image server 4. For the computer process. AI (artificial intelligence) analysis utilizing AI is used that detects a lesion candidate region through CAD (Computer Aided Diagnosis) and performs image diagnosis and image analysis, for example.

Figure 3:
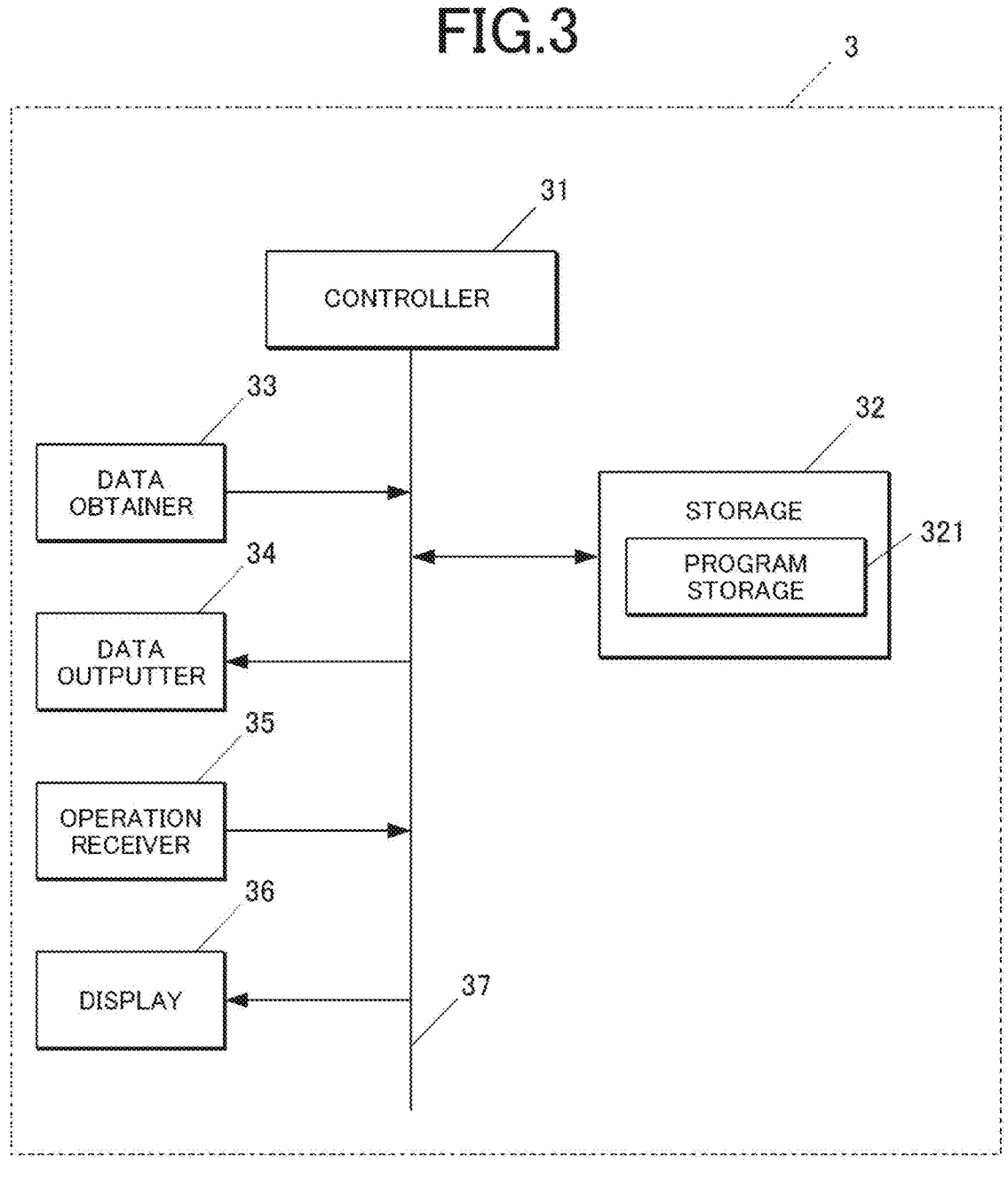
FIG. 3 is a block diagram illustrating a functional configuration of an analysis apparatus.

FIG. 3 is a block diagram illustrating a functional configuration of the analysis apparatus 3.

As illustrated in FIG. 3, the analysis apparatus 3 includes a controller 31 (first hardware processor), a storage 32, a data obtainer 33, a data outputter 34, an operation receiver 35, and a display 36, which are connected by a bus 37.

The controller 31 includes a central processing unit (CPU), and a random access memory (RAM), and centrally controls operations by the components of the analysis apparatus 3. Specifically, the CPU reads various processing programs stored in a program storage 321 of the storage 32 and loads the programs into the RAM, and executes various processes according to the programs. The controller 31 executes processes in the analysis apparatus 3 in a sequence illustrated in FIG. 5, thus functioning as a first obtainer, a second obtainer, a converter, and a generator.

Figure 5:
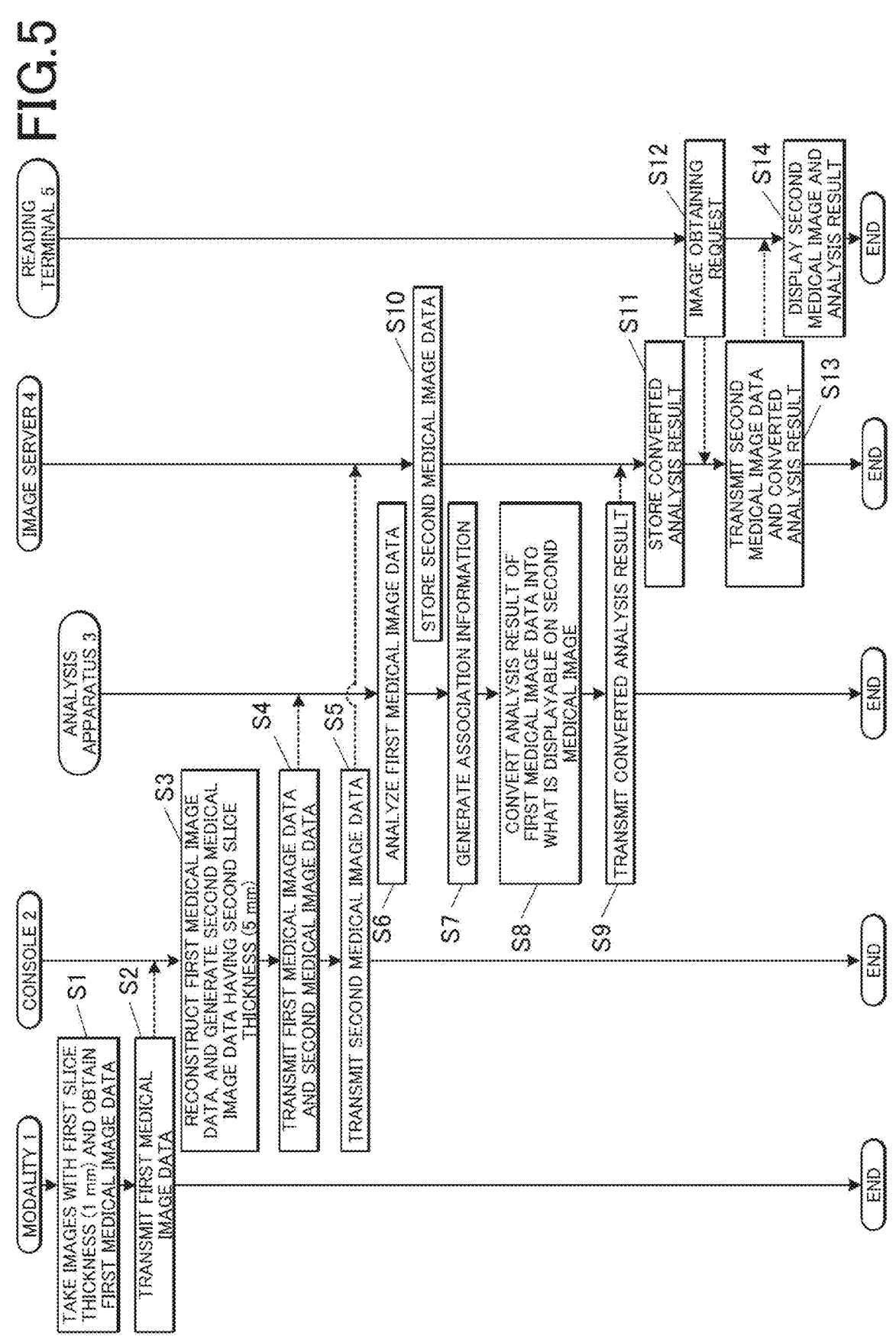
FIG. 5 is a sequence diagram illustrating a flow from image taking to image displaying in a first embodiment.

The storage 32 includes a hard disk drive (HDD) and a semiconductor memory, and further includes the program storage 321 that stores programs for executing various processes that include programs for executing processes in the analysis apparatus 3 in the sequence illustrated in FIG. 5, and programs for analysis. The storage 32 stores parameters and files required to execute the programs stored in the program storage 321.

The data obtainer 33 is configured as a network interface or the like, for example, and is configured to receive data from external equipment connected in a wired or wireless manner through the communication network N. Note that in tins embodiment, the data obtainer 33 is configured as a network interface or the like, but may also be configured as a port or the like into which a USB memory, an SD card or the like can be inserted.

The data outputter 34 is configured as a network interface or the like, for example, and is configured to output data to external equipment connected in a wired or wireless manner through the communication network N. Note that in this embodiment, the data outputter 34 is assumed to be configured as the network interface or the like. Alternatively, a connecter for connection to external equipment, and ports for various media, such as a USB memory, are applicable.

The operation receiver 35 includes a keyboard provided with various keys, and a pointing device, such as a mouse, or a touch panel attached to the display 36. The operation receiver 35 allows a user to perform input operations, and specifically, outputs, to the controller 31, an operation signal input via a key operation on the keyboard, a mouse operation, or a touch operation on the touch panel.

The display 36 includes a monitor, such as a liquid crystal display (LCD), and displays various screens according to instructions in a display signal input from the controller 31. Note that the number of monitors is not limited to one. A plurality of monitors may be provided instead.

The analysis apparatus 3 may be a type of an apparatus that outputs the first medical image data and the generated analysis result (analysis result data) to the reading terminal 5, and allows a doctor to verify the analysis result on the reading terminal 5, and finally determines the analysis result if the verification is affirmative. Alternatively, this apparatus may be a gateway type apparatus that adopts the generated analysis result itself as the analysis result of the first medical image data without verification by a doctor.

The image server 4 is, for example, a server for the PACS, and is an image management apparatus that stores and manages second medical image data output from the console 2.

Figure 4:
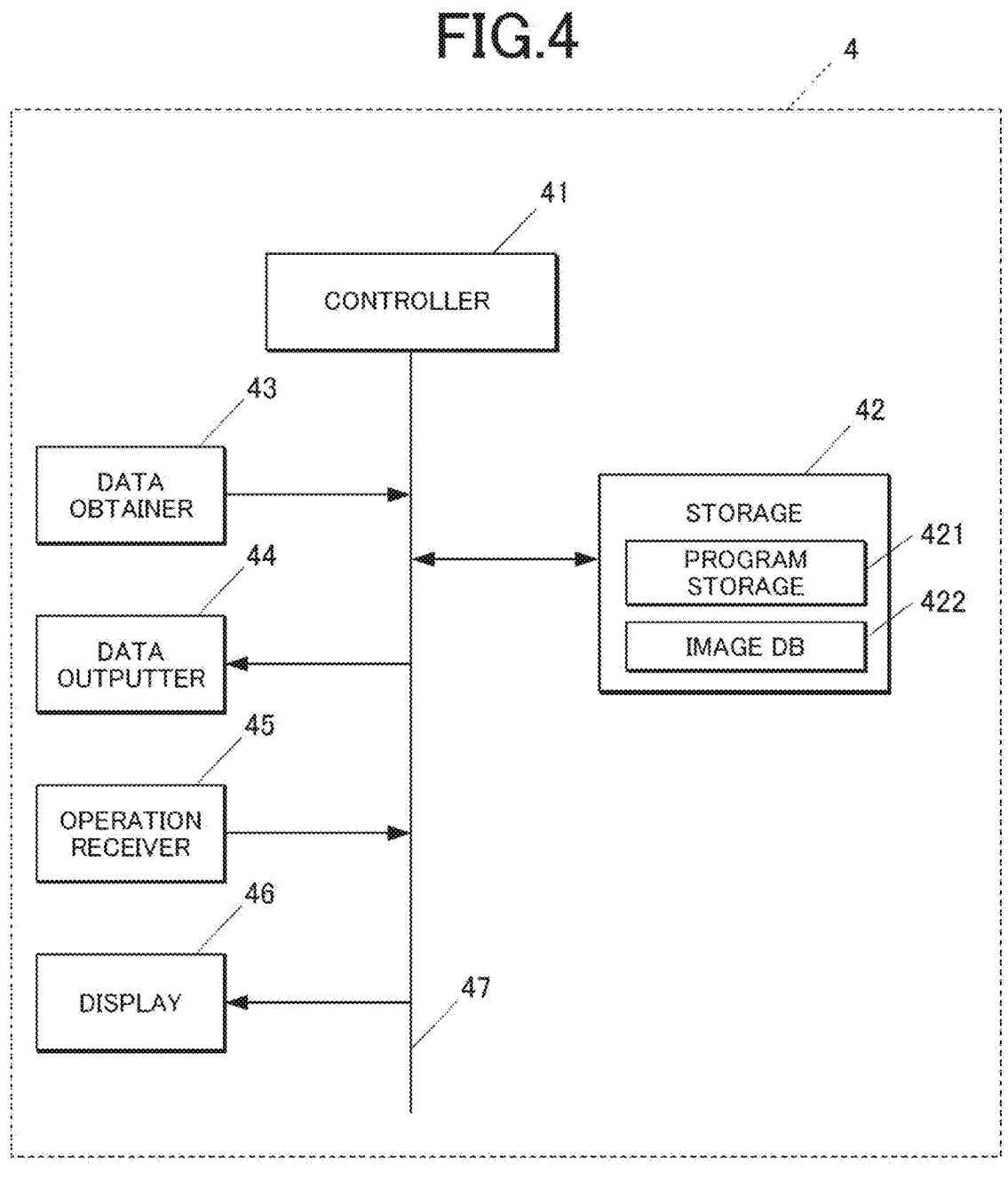
FIG. 4 is a block diagram illustrating a functional configuration of an image server.

FIG. 4 is a block diagram illustrating a functional configuration of the image server 4.

As illustrated in FIG. 4, the image server 4 includes a controller 41 (second hardware processor), a storage 42, a data obtainer 43, a data outputter 44, an operation receiver 45, and a display 46, which are connected by a bus 47.

The controller 41 includes a CPU (central processing unit) and a RAM (random access memory), and centrally controls operations by the components of the image server 4. Specifically, the CPU reads various processing programs stored in a program storage 421 of the storage 42 and loads the programs into the RAM, and executes various processes according to the programs.

The storage 42 includes a hard disk drive (HDD) and a semiconductor memory, and further includes the program storage 421 that stores programs for executing various processes that include programs for executing processes in the image server 4 in the sequence illustrated in FIG. 5. The storage 42 stores parameters and files required to execute the programs stored in the program storage 421.

The storage 42 includes an image database (DB) 422. The image DB 422 is a database for storing the second medical image data transmitted from the console 2, and an analysis result (an analysis result by the analysis apparatus 3) converted into what is displayable on the second medical image. The image DB 422 includes an image management table that stores management information (auxiliary information) on the second medical image data stored in the image DB 422. The image management table stores, for example, pieces of information that are the patient information, the test information, the image identification information, the image position information, and identification information on the analysis result (e.g., the file name of a grayscale softcopy presentation state (GSPS) file etc.), on each slice image data item of the second medical image data.

The data obtainer 43 is configured as a network interface or the like, for example, and is configured to receive data from external equipment connected in a wired or wireless manner through the communication network N. Note that in this embodiment, the data obtainer 43 is configured as a network interface or the like, but may also be configured as a port or the like into which a USB memory, an SD card or the like can be inserted.

The data outputter 44 is configured as a network interface or the like, for example, and is configured to output data to external equipment connected in a wired or wireless manner through the communication network N. Note that in this embodiment, the data outputter 44 is assumed to be configured as the network interface or the like. Alternatively, a connecter for connection to external equipment, and ports for various media, such as a USB memory, are applicable.

The operation receiver 45 includes a keyboard provided with various keys, and a pointing device, such as a mouse, or a touch panel attached to the display 46. The operation receiver 45 allows a user to perform input operations, and specifically, outputs, to the controller 41, an operation signal input via a key operation on the keyboard, a mouse operation, or a touch operation on the touch panel.

The display 46, which includes a monitor such as a liquid crystal display (LCD), displays various kinds of screens in accordance with an instruction of a display signal input from the controller 41. Note that the number of monitors is not limited to one. A plurality of monitors may be provided instead.

The reading terminal 5 is, for example, a client (PACS viewer) of the PACS, and is a display apparatus that reads, from the image server 4 or the like, the second medical image data, and the analysis result converted into what is displayable on the second medical image, and displays them for allowing reading. The reading terminal 5 includes a controller, a display, an operation receiver, a communicator, and a storage, which are not illustrated.

[Configuration of Image Display System 100]

Next, operation of an image display system 100 is described.

FIG. 5 is a sequence diagram illustrating the flow from image taking to image displaying in the image display system 100. Hereinafter, referring to FIG. 5, the flow from image taking to image displaying in the image display system 100 is described.

First, the modality 1 takes images with a first slice thickness (I mm) and obtains first medical image data, based on the test order information (Step S1), and transmits the first medical image data to the console 2 (Step S2).

Upon reception of the first medical image data, the console 2 reconstructs the first medical image data, and generates second medical image data having the second slice thickness (5 mm) (Step S3).

The console 2 then transmits the first medical image data and the second medical image data to the analysis apparatus 3 (Step S4), and transmits the second medical image data to the image server 4 (Step S5).

In the analysis apparatus 3, the controller 31 causes the data obtainer 33 to obtain the first medical image data and the second medical image data transmitted from the console 2, and analyzes the first medical image data and generates (obtains) an analysis result (Step S6).

Specifically, through cooperation with the programs for analysis (e.g., a learned model) stored in the program storage 321, the controller 31 analyzes each of slice image data items in the first medical image data, detects a lesion candidate region, and generates the analysis result that includes image identification information (UID and the instance number) on the detection-source slice image data item, the image position information (X coordinate, Y coordinate, and Z coordinate) in the detected lesion candidate region, a lesion type, and annotation information. If the same lesion candidate region is imaged continuously between a plurality of slice image data items, the analysis result is generated with respect to a slice image data item where the lesion candidate region is most largely taken (representative slice image data item). For example, the analysis result is generated in conformity with the GSPS format, and temporarily stored in the RAM of the controller 31 or the storage 32.

Next, the controller 31 of the analysis apparatus 3 generates association information for converting the analysis result of the first medical image data into what is displayable on the second medical image based on the second medical image data, on the basis of an association relationship between image position information on the first medical image data, and image position information on the second medical image data (Step S7).

As described above, the analysis apparatus 3 generates the analysis result, based on the first medical image data having the first slice thickness (1 mm). Meanwhile, the image server 4 stores the second medical image data having the second slice thickness (5 mm), and the reading terminal 5 displays the second medical image data. Analysis is performed based on the first medical image data having the thin slice thickness because the thinner the slice thickness is, the easier a minute lesion can be detected. The second medical image data having the large slice thickness is provided for reading because the larger the slice thickness is, the smaller the number of medical image data items is, thus improving the reading efficiency and allowing the storage capacity in use to be small.

However, for the analysis result of the first medical image data, the image data item where the analysis result is displayed is identified by the instance number and UID of the detection-source slice in the first medical image data. Accordingly, the annotation information indicating the analysis result cannot be displayed on the second medical image based on the second medical image data (it is unknown which slice image data item is associated).

In Step S7, the controller 31 generates association information for converting the analysis result of the first medical image data into what is displayable on the second medical image based on the second medical image data.

For example, the controller 31 generates the association information according to the following (1) to (5).

(1) The instance number and the image position information are obtained from the auxiliary information on each slice image data item in the first medical image data, the combination of the obtained instance number and the image position information is associated with Thin No. n (n; 1 . . . N; N is the number of slice image data items) in the order of instance numbers (see FIG. 6).

(2) The instance number and the image position information are obtained from the auxiliary information on each slice image data item in the second medical image data, the combination of the obtained instance number and the image position information is associated with Thick No. m (m; 1 . . . M; M is the number of slice image data items) in the order of instance numbers (see FIG. 7).

(3) Based on the association relationship between the numerical values of the Z coordinates of the image position information on the first medical image data and the image position information on the second medical image data, the slice image data items (Thick No. m) in the second medical image data that include a range imaged as slice image data items (Thin No. n) in the first medical image data are identified. Thus, the instance numbers of the slice image data items in the first medical image data are associated with the instance numbers of the slice image data items in the second medical image data.

For example, in a case where the Z coordinate of the image position information with the instance number=2 of the slice image data item in the first medical image data is −341, the Z coordinate of the image position information with the instance number=1 of the slice image data item in the second medical image data is −340, and the Z coordinate of the image position information with the instance number=2 is −345, the slice image data item with the instance number=2 in the first medical image data is associated with the slice image data item with the instance number=1 in the second medical image data.

(4) According to the association of (3), association information that associates Thin No. of the first medical image data and Thick No. of the second medical image data with each other (see FIG. 8) is generated.

(5) The generated association information is stored in the storage 32.

After the generation of the association information is finished, the controller 31 of the analysis apparatus 3 convents the analysis result of the first medical image data into what is displayable on the second medical image based on the second medical image data, on the basis of the generated association information (Step S8).

For example, the controller 31 converts the analysis result of the first medical image data into what is displayable on the second medical image based on the second medical image data, according to the following (1) to (4).

(1) Based on the instance number of the analysis result of the first medical image data, Thin No. is obtained.

(2) With reference to the association information. Thick No. associated with the obtained Thin No. is obtained.

(3) The image identification information on the slice image data item in the second medical image data associated with the obtained Thick No is obtained.

(4) The image identification information on the analysis result of the first medical image data is rewritten with the image identification information obtained in (3).

According to the process in Step S8, the analysis result of the first medical image data is displayable on the second medical image based on the second medical image data.

Note that the slice image data in the first medical image data is associated with the slice image data in the second medical image data, thus associating multiple slice image data items in the first medical image data with one slice image data item in the second medical image data, as illustrated in FIG. 8. That is, a plurality of analysis results are associated with a single slice image data item in the second medical image data (converted into what is displayable). However, in this case, management of the analysis results associated with the second medical image data possibly becomes cumbersome.

Accordingly, the analysis results to be associated with the same slice image data item in the second medical image data may be integrated into one analysis result.

Figure 9:
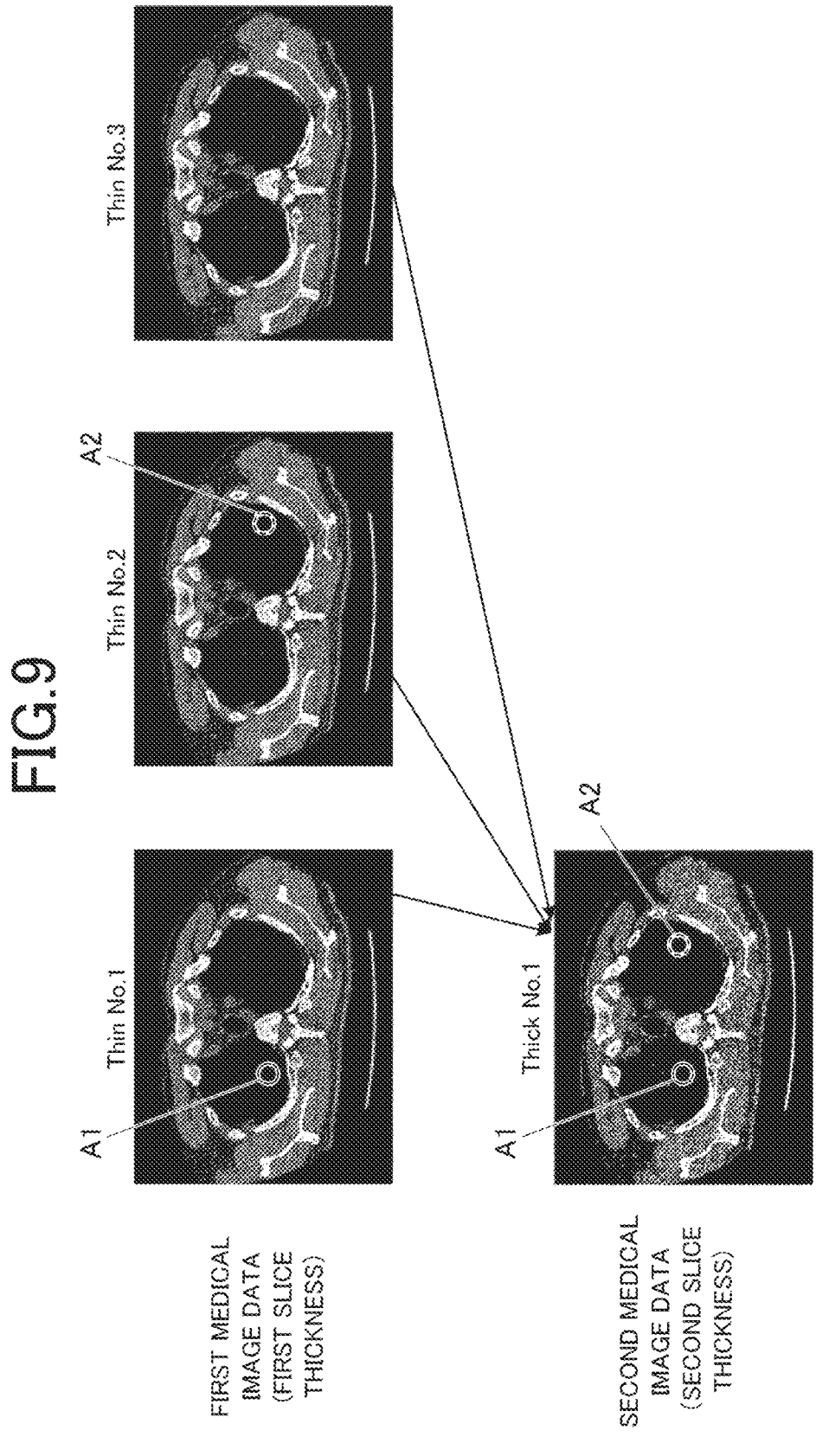
FIG. 9 illustrates an example of associating a plurality of analysis results with one slice image data item.

For example, as illustrated in FIG. 9, in a case where the slice images of Thin Nos. 1 to 3 in the first medical image data are associated with the slice image of Thick No. 1 in the second medical image data, analysis results of the slice images having Thin Nos. 1 to 3 may be integrated into one analysis result (for example, in any one of the analysis results, the other analysis results are written), and the image identification information on the integrated analysis result is replaced with image identification information on the slice image data item having Thick No. 1. Accordingly, for example, an analysis result of Thick No. 1 illustrated in FIG. 9 becomes one data item (file) that includes information on a lesion candidate region A1 (the image position information, lesion type, and annotation information) detected from Thin No. 1, information on a lesion candidate region A2 (the image position information, lesion type, and annotation information) detected from Thin No. 2.

Thus, the slice image data in the second medical image data, and the analysis result data are associated on a one-to-one basis.

Next, the controller 31 of the analysis apparatus 3 transmits the analysis result converted into what is to be displayed on the second medical image is transmitted by the data outputter 34 to the image server 4 (Step S9).

In the image server 4, the controller 41 causes the data obtainer 43 to obtain the second medical image data transmitted from the console 2, and stores the obtained second medical image data in the image DB 422 (Step S10).

That is, the controller 41 stores the slice image data items in the obtained second medical image data in the image DB 422, and writes their auxiliary information in the image management table.

In the image server 4, the controller 41 causes the data obtainer 43 to obtain the analysis result (analysis result converted into what is to be displayed on the second medical image) transmitted from the analysis apparatus 3, and stores the obtained analysis result in the image DB 422 (Step S11).

That is, the controller 41 saves the file of the obtained analysis result in the image DB 422, and writes identification information (GSPS file name etc.) on the obtained analysis result, in a record having UID included in the analysis result in the image DB 422.

Through the reading terminal 5, test information and the like on the second medical image data stored in the image DB 422 is designated, and image obtaining request for the designated test is transmitted to the image server 4 (Step S12), and the controller 41 of the image server 4 reads the second medical image data on the designated test, and the associated analysis result, from the image DB 422, and causes the data outputter 44 to transmit them to the reading terminal 5 (Step S13).

Upon reception of the second medical image data and the analysis result from the image server 4, the reading terminal 5 displays, on the display, the second medical image based on the received second medical image data, while adding the annotation information indicating the analysis result on the second medical image and thus displaying the image (Step S14).

The user studies the displayed second medical image and analysis result, and executes reading.

The above description is a sequence from image taking to image displaying in the image display system 100.

The reading terminal 5 is provided with the analysis result converted into what is displayable on the second medical image based on the second medical image data. Accordingly, the analysis result can be displayed on a correct slice image among the second medical images.

Second Embodiment

Next, a second embodiment of the present invention will be described.

According to the second embodiment, an example is described where the analysis apparatus 3 generates the association information described above and outputs this information to the image server 4, and the image server 4 converts the analysis result of the first medical image data into what is displayable on the second medical image based on the second medical image data on the basis of the obtained association information.

Figure 10:
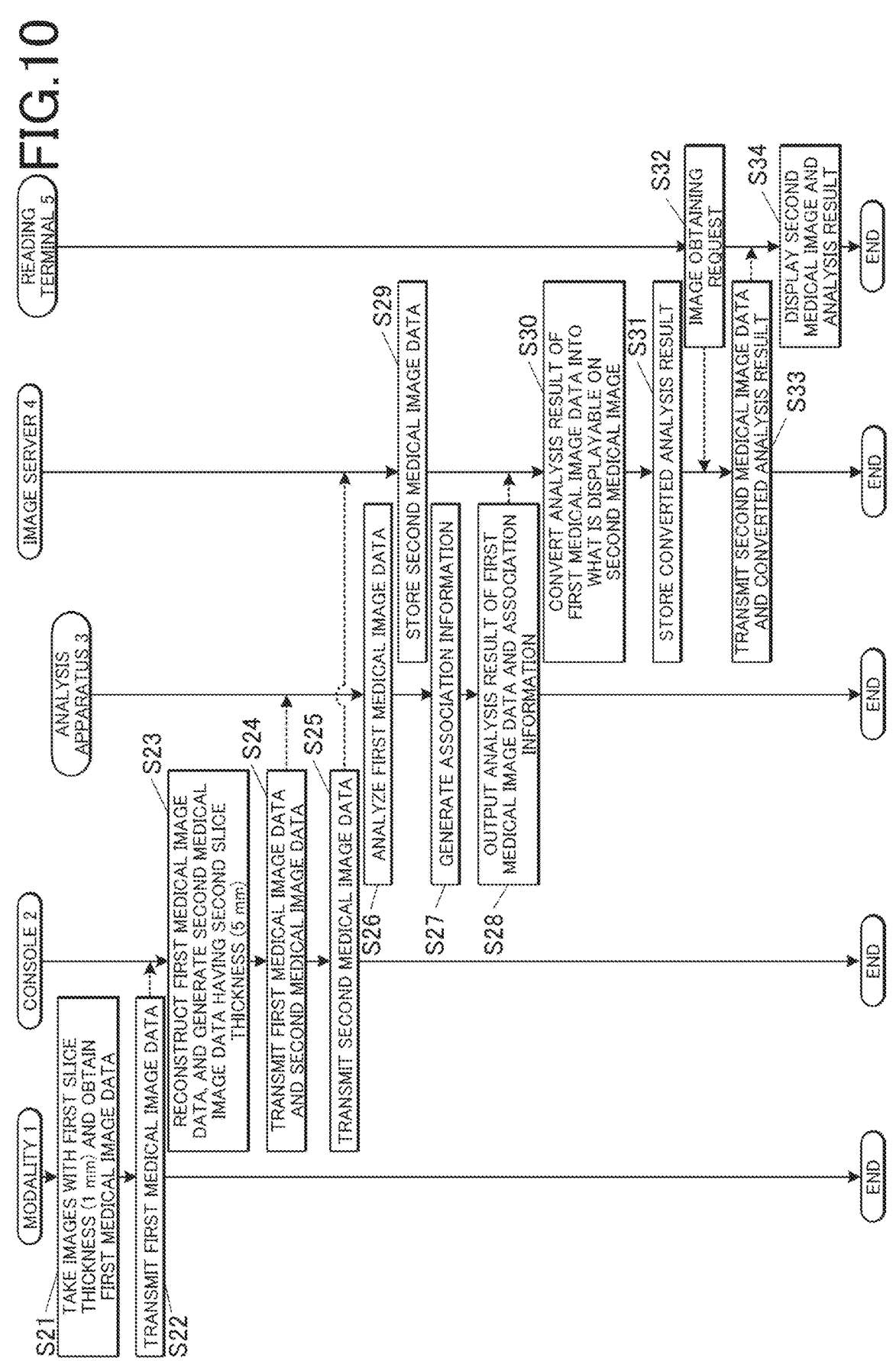
FIG. 10 is a sequence diagram illustrating a flow from image taking to image displaying in a second embodiment.

In the second embodiment, the program storage 321 of the analysis apparatus 3 stores programs for executing the processes in the analysis apparatus 3 in the sequence illustrated in FIG. 10. Through cooperation with the programs stored in the storage 32, the controller 31 executes the processes in the analysis apparatus 3 in the sequence illustrated in FIG. 10. The controller 31 executes the processes in the analysis apparatus 3 in the sequence illustrated in FIG. 10, thus functioning as an output device.

The program storage 421 of the image server 4 stores programs for executing the processes in the image server 4 in the sequence illustrated in FIG. 10. Through cooperation with the programs stored in the storage 42, the controller 41 executes the processes in the image server 4 in the sequence illustrated in FIG. 10. The controller 41 executes the processes in the image server 4 in the sequence illustrated in FIG. 10, thus functioning as the first obtainer, the second obtainer, a third obtainer, and the converter.

The other components of the image display system 100 are similar to those described in the first embodiment. Accordingly, the description applies to them. Hereinafter, operation in the second embodiment is described.

FIG. 10 is a sequence diagram illustrating the flow from image taking to image displaying in the image display system 100 in the second embodiment. Hereinafter, referring to FIG. 10, the flow from image taking to image displaying in the image display system 100 in the second embodiment is described.

First, the modality 1 takes images with a first slice thickness (1 mm) and obtains first medical image data, based on the test order information (Step S21), and transmits the first medical image data to the console 2 (Step S22).

Upon reception of the first medical image data, the console 2 reconstructs the first medical image data, and generates second medical image data having the second slice thickness (5 mm) (Step S23).

The console 2 then transmits the first medical image data and the second medical image data to the analysis apparatus 3 (Step S24), and transmits the second medical image data to the image server 4 (Step S25).

In the analysis apparatus 3, the controller 31 causes the data obtainer 33 to obtain the first medical image data and the second medical image data transmitted from the console 2, and analyzes the first medical image data and generates (obtains) an analysis result (Step S26).

The process of Step S26 is similar to that described in Step S6 in FIG. 5. Accordingly, the description applies.

Next, the controller 31 of the analysis apparatus 3 generates association information for converting the analysis result of the first medical image data into what is displayable on the second medical image based on the second medical image data, on the basis of an association relationship between image position information on the first medical image data, and image position information on the second medical image data (Step S27).

The process of Step S27 is similar to that described in Step S7 in FIG. 5. Accordingly, the description applies.

After the generation of the association information is finished, the controller 31 of the analysis apparatus causes the data outputter 34 to output the analysis result of the first medical image data and the association information to the image server 4 (Step S28).

In the image server 4, the controller 41 causes the data obtainer 43 to obtain the second medical image data transmitted from the console 2, and stores the obtained second medical image data in the image DB 422 (Step S29).

The process of Step S29 is similar to that of Step S10 in FIG. 5. Accordingly, the description applies.

In the image server 4, the controller 41 causes the data obtainer 43 to obtain the analysis result of the first medical image data and the association information output from the analysis apparatus 3, and converts the obtained analysis result of the first medical image data into what is displayable on the second medical image based on the second medical image data on the basis of the obtained association information (Step S30).

The process of Step S30 is similar to that described in Step S8 in FIG. 5. Accordingly, the description applies.

The controller 41 of the image server 4 stores, in the image DB 422, the analysis result converted into what is displayable on the second medical image (Step S31).

The process of Step S31 is similar to that described in Step S11 in FIG. 5. Accordingly, the description applies.

Through the reading terminal 5, test information and the like on the second medical image data stored in the image DB 422 is designated, and image obtaining request for the designated test is transmitted to the image server 4 (Step S32), and the controller 41 of the image server 4 reads the second medical image data on the designated test, and the associated analysis result, from the image DB 422, and causes the data outputter 44 to transmit them to the reading terminal 5 (Step S33).

Upon reception of the second medical image data and the analysis result from the image server 4, the reading terminal 5 displays, on the display, the second medical image based on the received second medical image data, while adding the annotation information indicating the analysis result on the second medical image and thus displaying the image (Step S34).

The user studies the displayed second medical image and analysis result, and executes reading.

The above description is the sequence from image taking to image displaying in the image display system 100 in the second embodiment.

The reading terminal 5 is provided with the analysis result converted into what is displayable on the second medical image based on the second medical image data. Accordingly, the analysis result can be displayed on a correct slice image among the second medical images.

Third Embodiment

Next, a third embodiment of the present invention will be described.

According to the third embodiment, an example is described where the image server 4 generates the association information, and converts the analysis result of the first medical image data into what is displayable on the second medical image based on the second medical image data.

In the third embodiment, the console 2 transmits the first medical image data to the analysis apparatus 3, and transmits the second medical image data to the image server 4.

Figure 11:
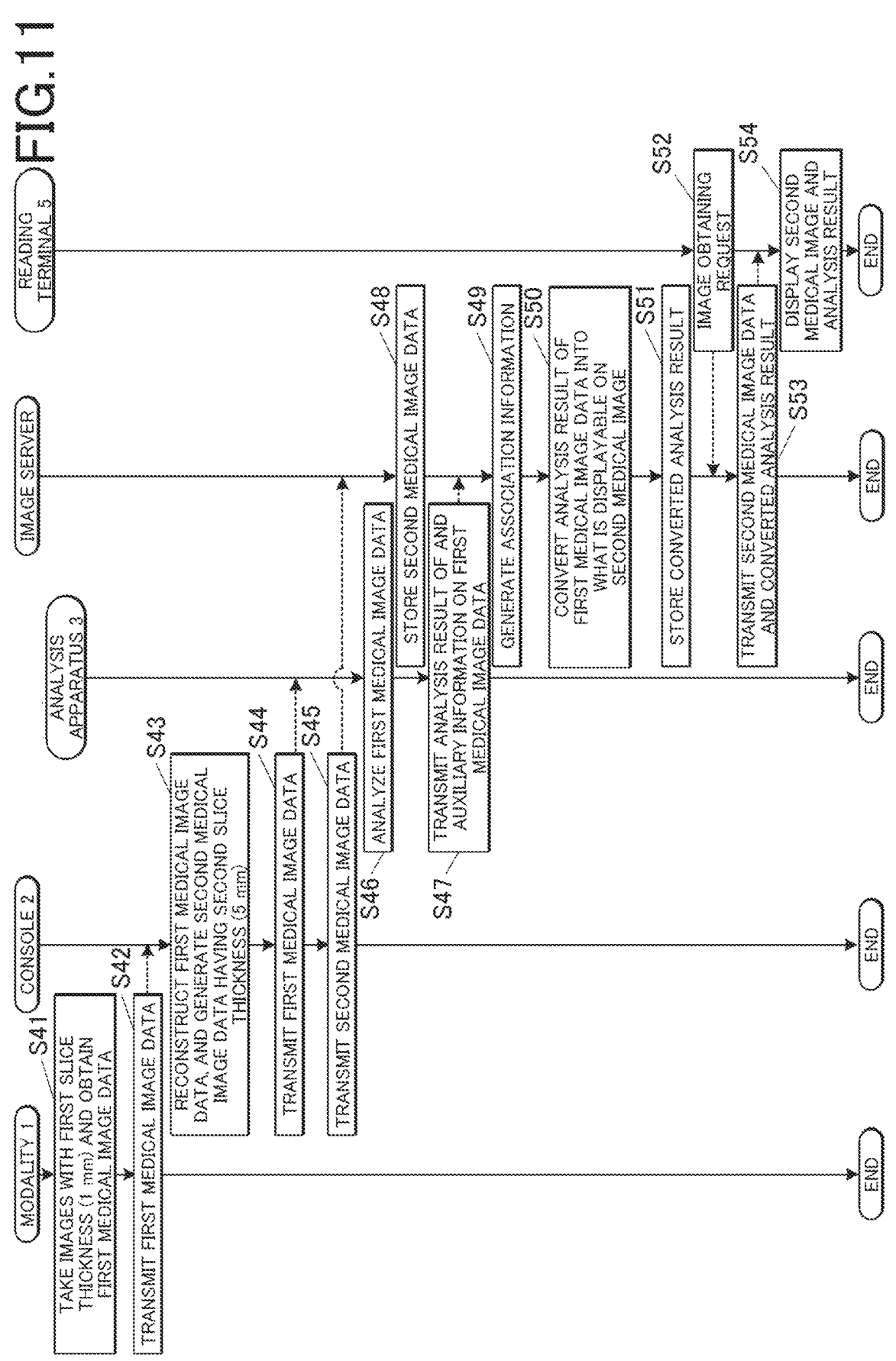
FIG. 11 is a sequence diagram illustrating a flow from image taking to image displaying in a third embodiment.

The program storage 321 of the analysis apparatus 3 stores programs for executing the processes in the analysis apparatus 3 in the sequence illustrated in FIG. 11. Through cooperation with the programs stored in the storage 32, the controller 31 executes the processes in the analysis apparatus 3 in the sequence illustrated in FIG. 11.

The program storage 421 of the image server 4 stores programs for executing the processes in the image server 4 in the sequence illustrated in FIG. 11. Through cooperation with the programs stored in the storage 42, the controller 41 executes the processes in the image server 4 in the sequence illustrated in FIG. 11. The controller 41 executes the processes in the image server 4 in the sequence illustrated in FIG. 11, thus functioning as the first obtainer, the second obtainer, the generator, and the converter.

The other components of the image display system 100 are similar to those described in the first embodiment. Accordingly, the description applies to them. Hereinafter, operation in the third embodiment is described.

FIG. 11 is a sequence diagram illustrating the flow from image taking to image displaying in the image display system 100 in the third embodiment. Hereinafter, referring to FIG. 11, the flow from image taking to image displaying in the image display system 100 in the third embodiment is described.

First, the modality 1 takes images with a first slice thickness (1 mm) and obtains first medical image data, based on the test order information (Step S41), and transmits the first medical image data to the console 2 (Step S42).

Upon reception of the first medical image data, the console 2 reconstructs the first medical image data, and generates second medical image data having the second slice thickness (5 mm) (Step S43).

The console 2 then transmits the first medical image data to the analysis apparatus 3 (Step S44), and transmits the second medical image data to the image server 4 (Step S45).

In the analysis apparatus 3, the controller 31 causes the data obtainer 33 to obtain the first medical image data transmitted from the console 2, and analyzes the obtained first medical image data and generates (obtains) an analysis result (Step S46).

The generation of the analysis result in Step S46 is similar to that described in Step S6 in FIG. 5. Accordingly, the description applies.

The controller 31 causes the data outputter 34 to transmit the generated analysis result, and the auxiliary information on each slice image data item in the first medical image data to the image server 4 (Step S47).

In the image server 4, the controller 41 causes the data obtainer 43 to obtain the second medical image data transmitted from the console 2, and stores the obtained second medical image data in the image DB 422 (Step S48).

The process of Step S48 is similar to that of Step S10 in FIG. 5. Accordingly, the description applies.

In the image server 4, the controller 41 causes the data obtainer 43 to obtain the analysis result of the first medical image data and the auxiliary information on each slice image data item in the first medical image data transmitted from the analysis apparatus 3, and generates association information for converting the analysis result of the first medical image data into what is displayable on the second medical image based on the second medical image data, on the basis of the association relationship between the image position information on the first medical image data and the image position information on the second medical image data (Step S49).

The generation of the association information in Step S49 is similar to that described in Step S7 in FIG. 5. Accordingly, the description applies.

Next, in the image server 4, the controller 41 converts the obtained analysis result of the first medical image data into what is displayable on the second medical image based on the second medical image data, on the basis of the generated association information (Step S50).

The process of Step S50 is similar to that described in Step S8 in FIG. 5. Accordingly, the description applies.

The controller 41 of the image server 4 stores, in the image DB 422, the analysis result converted into what is displayable on the second medical image (Step S51).

The process of Step SSI is similar to that described in Step S11 in FIG. 5. Accordingly, the description applies.

Through the reading terminal 5, test information and the like on the second medical image data stored in the image DB 422 is designated, and image obtaining request for the designated test is transmitted to the image server 4 (Step S52), and the controller 41 of the image server 4 reads the second medical image data on the designated test, and the associated analysis result, from the image DB 422, and causes the data outputter 44 to transmit them to the reading terminal 5 (Step S53).

Upon reception of the second medical image data and the analysis result from the image server 4, the reading terminal 5 displays, on the display, the second medical image based on the received second medical image data, while adding the annotation information indicating the analysis result on the second medical image and thus displaying the image (Step S54).

The user studies the displayed second medical image and analysis result, and executes reading.

The above description is a sequence from image taking to image displaying in the image display system 100 in the third embodiment.

The reading terminal 5 is provided with the analysis result converted into what is displayable on the second medical image based on the second medical image data. Accordingly, the analysis result can be displayed on a correct slice image among the second medical images.

Note that in the third embodiment described above, it is assumed that the image server 4 obtains, from the analysis apparatus 3, the auxiliary information on the first medical image data required to generate the association information. Alternatively, the auxiliary information may be obtained from the console 2. Further alternatively, although a certain transmission time period is required, the image server 4 may obtain the first medical image data from the analysis apparatus 3 or the console 2.

Modification

In the first to third embodiments, the association information is generated every time the first medical image data and the second medical image data are generated, and the analysis result of the first medical image data is converted into what is displayable on the second medical image based on the second medical image data on the basis of the association information. Alternatively, for example, in a case where the first slice thickness, the second slice thickness, and the image position and the imaging range of the first slice image in the first medical image data taken by the modality 1 (with respect to each site) are fixed, association information having already been generated may be preliminarily stored in the storage 32 of the analysis apparatus 3 or the storage 42 of the image server 4, and the controller 31 of the analysis apparatus 3 or the controller 41 of the image server 4 may convert the analysis result of the first medical image data into what is displayable on the second medical image based on the second medical image data on the basis of the stored association information.

Alternatively, without generation of the association information, on the basis of information on the first slice thickness and the second slice thickness, the analysis result of the first medical image data may be converted into what is displayable on the second medical image based on the second medical image data.

For example, the controller 31 of the analysis apparatus 3 or the controller 41 of the image server 4 calculates the pieces of image position information on the slice image data items in the first medical image data and the second medical image data, on the basis of the information on the first slice thickness and the second slice thickness and of the image position information on the first slice image of the first medical image data or the second medical image data, and identifies the instance number of the second medical image data associated with the instance number of the analysis result of the first medical image data, on the basis of the calculated image position information. The image identification information on the analysis result of the first medical image data is then rewritten with the image identification information on the slice image data item having the identified instance number. Accordingly, the analysis result of the first medical image data can be converted into what is displayable on the second medical image based on the second medical image data.

The process of converting the analysis result of the first medical image data into what is displayable on the second medical image based on the second medical image data may be performed by the controller of the reading terminal 5.

For example, in the image server 4, the controller 41 stores, in the storage 42, the analysis result of the first medical image data, and the association information obtained from the analysis apparatus 3 or generated in the image server 4, in association with the second medical image data stored in the image DB 422 (for example, associated by the patient information, the test information, etc.), and transmits the analysis result of the first medical image data, and the association information together with the second medical image data associated with the designated test information, to the reading terminal 5, in response to the image obtaining request issued by the reading terminal 5. The reading terminal 5 converts the analysis result of the first medical image data into what is displayable on the second medical image based on the second medical image data, on the basis of the association information obtained from the image server 4, and displays the analysis result on the second medical image based on the second medical image data.

Alternatively, in the image server 4, the controller 41 stores, in the storage 42, the analysis result of the first medical image data, and the auxiliary information on each slice image data item in the first medical image data in association with the second medical image data stored in the image DB 422 (for example, associated by the patient information, the test information, etc.), and transmits the analysis result of the first medical image data, and the auxiliary information together with the second medical image data associated with the designated test information, to the reading terminal 5, in response to the image obtaining request issued by the reading terminal 5. The reading terminal 5 generates the association information on the basis of the obtained second medical image data, the analysis result of the first medical image data, and the auxiliary information, or identifies the instance number of the second medical image data associated with the instance number included in the analysis result of the first medical image data on the basis of the first slice thickness and the second slice thickness, and converts the analysis result of the first medical image data into what is displayable on the second medical image based on the second medical image data.

Note that the process of generating the association information, the process of converting the analysis result of the first medical image data into what is displayable on the second medical image based on the second medical image data, using the association information, and the process of converting the analysis result of the first medical image data into what is displayable on the second medical image based on the second medical image data without using the association information are similar to those described in the first to third embodiments.

As described above, the image display system 100 obtains the analysis result acquired by a computer process for the first medical image data having the first slice thickness, obtains the second medical image data reconstructed, from the obtained first medical image data, to have the second slice thickness different from the first slice thickness, and converts the analysis result of the first medical image data into what is displayable on the second medical image based on the second medical image data.

Accordingly, the analysis result acquired by the computer process for first medical image data having the first slice thickness is allowed to be displayed on the second medical image reconstructed to have the second slice thickness different from the first slice thickness.

Note that the present invention is not limited to the embodiments described above, and can be variously modified in a range without departing from the gist.

For example, according to the aforementioned embodiment, the case of obtaining the analysis result of the first medical image data in the GSPS format is described as example. There is no limitation to this. The SR (Structured Report) format may be adopted.

The controller 31 and the controller 41 may include a device that converts the analysis result of the first medical image data into what is displayable on the second medical image based on the second medical image data, and subsequently generates embedded image data where the analysis result is embedded in the second medical image data (e.g., an annotation indicating a lesion candidate region). That is, the program causing a computer (e.g., the controller 31 or the controller 41) to achieve the function of converting the analysis result of the first medical image data into what is displayable on the second medical image based on the second medical image data may include a program causing the computer to achieve a function of converting the analysis result of the first medical image data into what is displayable on the second medical image based on the second medical image data, and subsequently generating embedded image data where the analysis result (e.g., an annotation indicating a lesion candidate region) is embedded in the second medical image data.

The embedded image data includes, for example, a screen capture image. For example, the analysis result of the first medical image data is converted into what is displayable on the second medical image based on the second medical image data, and subsequently the screen capture image where the analysis result (e.g., an annotation indicating a lesion candidate region) is displayed on a medical image based on the second medical image data is generated in the memory, thus allowing the embedded image data to be generated.

By generating the embedded image data as the analysis result after conversion, the analysis result can be simply displayed on the reading terminal 5. On the other hand, in the cases of the GSPS format and the SR format, the annotation information is required to be overlaid on an original image in accordance with user operation. Accordingly, efforts of the user operation, and a process of over-laying the analysis result on the image occur.

In the embodiment described above, in FIG. 1, the analysis apparatus 3, the image server 4, and the reading terminal 5 are illustrated as separate and independent apparatuses. Alternatively, the image server 4 and the reading terminal 5 may be configured as an integrated apparatus, this integrated configuration may apply to the analysis apparatus 3 and the image server 4, and also to the analysis apparatus 3, the image server 4 and the reading terminal 5.

The first obtainer, the second obtainer, the third obtainer, the output device and the generator of the image display system according to the present invention may be distributed in a plurality of apparatuses.

In the above description, the example is disclosed where the hard disk, the semiconductor nonvolatile memory or the like is used as a computer-readable medium for the program according to the present invention. However, there is no limitation to this example. As another computer-readable medium, a portable recording medium, such as a CD-ROM, may be applied. Carrier waves are also applicable as a medium of providing data on the program according to the present invention via a communication line.

Furthermore, detailed configurations and detailed operation of the apparatuses that constitute the image display system can be changed as appropriate within a range not deviating from the spirit of the invention.

Although embodiments of the present invention have been described and illustrated in detail, the disclosed embodiments are made for purposes of illustration and example only and not limitation. The scope of the present invention should be interpreted by terms of the appended claims.

The invention claimed is:

1. An image display system, comprising:
a first hardware processor configured to execute processes comprising:
    obtaining an analysis result acquired by performing a computer-based analysis process with respect to first medical image data having a first slice thickness;
    obtaining second medical image data reconstructed from the first medical image data, the second medical image data having a second slice thickness different from the first slice thickness;
    converting the analysis result obtained with respect to the first medical image data into data displayable on a second medical image based on the second medical image data;
    generating association information for converting the analysis result obtained with respect to the first medical image data into the data displayable on the second medical image, based on an association relationship between image position information on the first medical image data and image position information on the second medical image data;
    outputting the association information; and
    generating embedded image data in which the analysis result is embedded in the second medical image data.

2. The image display system according to claim 1, further comprising:
a second hardware processor configured to execute processes comprising:
    obtaining the association information, and
    converting the analysis result into the data displayable on the second medical image, based on the association information.

3. An image display system, comprising:
a first hardware processor configured to execute processes comprising:
    obtaining an analysis result acquired by performing a computer-based analysis process with respect to first medical image data having a first slice thickness;
    obtaining second medical image data reconstructed from the first medical image data and having a second slice thickness different from the first slice thickness;
    generating association information for converting the analysis result obtained with respect to the first medical image data into data displayable on a second medical image based on the second medical image data, based on an association relationship between image position information on the first medical image data and image position information on the second medical image data;
    outputting the association information; and
    generating embedded image data in which the analysis result is embedded in the second medical image data.

4. An analysis apparatus, comprising:
a first hardware processor configured to execute processes comprising:
    obtaining an analysis result acquired by performing a computer-based analysis process with respect to first medical image data having a first slice thickness;
    obtaining second medical image data reconstructed from the first medical image data, the second medical image data having a second slice thickness different from the first slice thickness;
    converting the analysis result obtained with respect to the first medical image data into data displayable on a second medical image based on the second medical image data;
    generating association information for converting the analysis result obtained with respect to the first medical image data into the data displayable on the second medical image, based on an association relationship between image position information on the first medical image data and image position information on the second medical image data;
    outputting the association information; and
    generating embedded image data in which the analysis result is embedded in the second medical image data.

5. An analysis apparatus, comprising:
a first hardware processor configured to execute processes comprising:
    obtaining an analysis result acquired by performing a computer-based analysis process with respect to first medical image data having a first slice thickness;

obtaining second medical image data reconstructed from the first medical image data, the second medical image data having a second slice thickness different from the first slice thickness;

generating association information for converting the analysis result obtained with respect to the first medical image data into data displayable on a second medical image based on the second medical image data, based on an association relationship between image position information on the first medical image data and image position information on the second medical image data;

outputting the association information; and generating embedded image data in which the analysis result is embedded in the second medical image data.

6. An image management apparatus, comprising:

a hardware processor configured to execute processes comprising:

obtaining an analysis result acquired by performing a computer-based analysis process with respect to first medical image data having a first slice thickness;

obtaining second medical image data reconstructed from the first medical image data, the second medical image data having a second slice thickness different from the first slice thickness;

converting the analysis result obtained with respect to the first medical image data into data displayable on a second medical image based on the second medical image data;

generating association information for converting the analysis result obtained with respect to the first medical image data into the data displayable on the second medical image, based on an association relationship between image position information on the first medical image data and image position information on the second medical image data;

outputting the association information; and generating embedded image data in which the analysis result is embedded in the second medical image data.

7. The image management apparatus according to claim 6, wherein the processes further comprise:

obtaining the association information, and converting the analysis result into the data displayable on the second medical image, based on the association information.

8. The image management apparatus according to claim 6, wherein the processes further comprise converting the analysis result into the data displayable on the second medical image based on the first slice thickness and the second slice thickness.

9. A non-transitory computer readable recording medium having a program stored thereon, the program being executable by a hardware processor of a computer to control the hardware processor to perform processes comprising:

obtaining an analysis result acquired by performing a computer-based analysis process with respect to first medical image data having a first slice thickness;

obtaining second medical image data reconstructed from the first medical image data, the second medical image data having a second slice thickness different from the first slice thickness;

converting the analysis result obtained with respect to the first medical image data into data displayable on a second medical image based on the second medical image data;

generating association information for converting the analysis result obtained with respect to the first medical image data into the data displayable on the second medical image, based on an association relationship between image position information on the first medical image data and image position information on the second medical image data;

outputting the association information; and generating embedded image data in which the analysis result is embedded in the second medical image data.

10. The recording medium according to claim 9, wherein the processes further comprise:

obtaining the association information, and converting the analysis result into the data displayable on the second medical image, based on the association information.

11. The recording medium according to claim 9, wherein:

the analysis result includes a plurality of analysis results, and the processes further comprise:

obtaining the plurality of analysis results; and converting the plurality of analysis results into the data displayable on the second medical image.

12. A non-transitory computer readable recording medium having a program stored thereon, the program being executable by a hardware processor of a computer to control the hardware processor to perform processes comprising:

obtaining an analysis result acquired by performing a computer-based analysis process with respect to first medical image data having a first slice thickness;

obtaining second medical image data reconstructed from the first medical image data and having a second slice thickness different from the first slice thickness;

generating association information for converting the analysis result obtained with respect to the first medical image data into data displayable on a second medical image based on the second medical image data, based on an association relationship between image position information on the first medical image data and image position information on the second medical image data;

outputting the association information; and generating embedded image data in which the analysis result is embedded in the second medical image data.

* * * * *